(12) United States Patent
Samaniuk et al.

(10) Patent No.: US 9,116,092 B2
(45) Date of Patent: Aug. 25, 2015

(54) DEVICE AND METHOD FOR MEASURING THE RHEOLOGICAL PROPERTIES OF A YIELD STRESS FLUID

(75) Inventors: Joseph R. Samaniuk, Madison, WI (US); Daniel J. Klingenberg, Stoughton, WI (US); Charles T. Scott, Mt. Horeb, WI (US); Thatcher W. Root, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 250 days.

(21) Appl. No.: 13/269,139

(22) Filed: Oct. 7, 2011

(65) Prior Publication Data

US 2013/0086979 A1 Apr. 11, 2013

(51) Int. Cl.
*G01N 11/14* (2006.01)
*G01N 11/00* (2006.01)

(52) U.S. Cl.
CPC ........ *G01N 11/14* (2013.01); *G01N 2011/0033* (2013.01); *G01N 2011/0053* (2013.01)

(58) Field of Classification Search
CPC .................................. G01N 3/08; G01N 11/14
USPC ............ 73/54.01, 54.23, 54.28, 54.35, 54.31, 73/760, 761, 788, 0.15, 789, 71, 826, 1.15, 73/81, 843
See application file for complete search history.

(56) References Cited

U.S. PATENT DOCUMENTS

| | | | | |
|---|---|---|---|---|
| 2,339,991 A * | 1/1944 | Hagy | | 73/54.35 |
| 2,625,034 A * | 1/1953 | Patterson, Jr. | | 73/54.23 |
| 4,630,468 A * | 12/1986 | Sweet | | 73/54.43 |
| 4,648,264 A * | 3/1987 | Freese et al. | | 73/64.41 |
| 5,142,900 A * | 9/1992 | Duke | | 73/54.39 |
| 5,167,143 A * | 12/1992 | Brookfield | | 73/54.23 |
| 5,365,777 A * | 11/1994 | Layton | | 73/54.28 |
| 6,065,330 A * | 5/2000 | Freeman et al. | | 73/54.28 |
| 6,167,752 B1 * | 1/2001 | Raffer | | 73/54.28 |
| 7,201,040 B2 * | 4/2007 | Bateson et al. | | 73/54.28 |
| 7,275,419 B2 * | 10/2007 | Raffer | | 73/54.28 |
| 7,412,877 B1 * | 8/2008 | Bi | | 73/54.28 |
| 7,624,625 B2 * | 12/2009 | Jau | | 73/54.31 |
| 7,992,427 B2 * | 8/2011 | Tonmukayakul et al. | ... | 73/54.28 |
| 8,313,229 B2 * | 11/2012 | Brannon et al. | | 366/142 |
| 2005/0138991 A1 * | 6/2005 | Wallevik et al. | | 73/54.02 |
| 2009/0133478 A1 * | 5/2009 | Sentmanat | | 73/54.28 |
| 2012/0210774 A1 * | 8/2012 | Raffer | | 73/54.28 |
| 2012/0234102 A1 * | 9/2012 | Johnson et al. | | 73/826 |

OTHER PUBLICATIONS

Pimenova et al, "Effect of Corn Stover Concentration on Rheological Characteristics," Applied Biochemistry and Biotechnology, vol. 113-116, p. 347-360, 2004.

(Continued)

*Primary Examiner* — Hezron E Williams
*Assistant Examiner* — Hoang Nguyen
(74) *Attorney, Agent, or Firm* — Boyle Fredrickson, S.C.

(57) ABSTRACT

A device and a method are provided for measuring the yield stress of a fluid. The device includes a container for receiving the fluid therein and an auger having a shaft extending along an axis and a helical flange extending radially about the shaft. The auger is movable in the fluid between a first position and a second position. A sensor is operatively connected to the auger. The sensor measures a force on the auger as the auger moves from the first position to the second position. A linkage is interconnected to the sensor. The linkage translates motion to the auger.

6 Claims, 4 Drawing Sheets

(56) References Cited

OTHER PUBLICATIONS

Thesis of Ehrhardt, "Rheology of Biomass," University of Wisconsin-Madison, 2008.

Knutsen et al, "Rheology of high-solids biomass slurries for biorefinery applications," J. Rheol. 53(4), 877-892, Jul./Aug. 2009.

Preliminary Report of Samaniuk, "Optimizing the Production of Biofuel by Controlling the Rheology of Lignocellulosic Biomass," University of Wisconsin-Madison, Feb. 15, 2010.

* cited by examiner

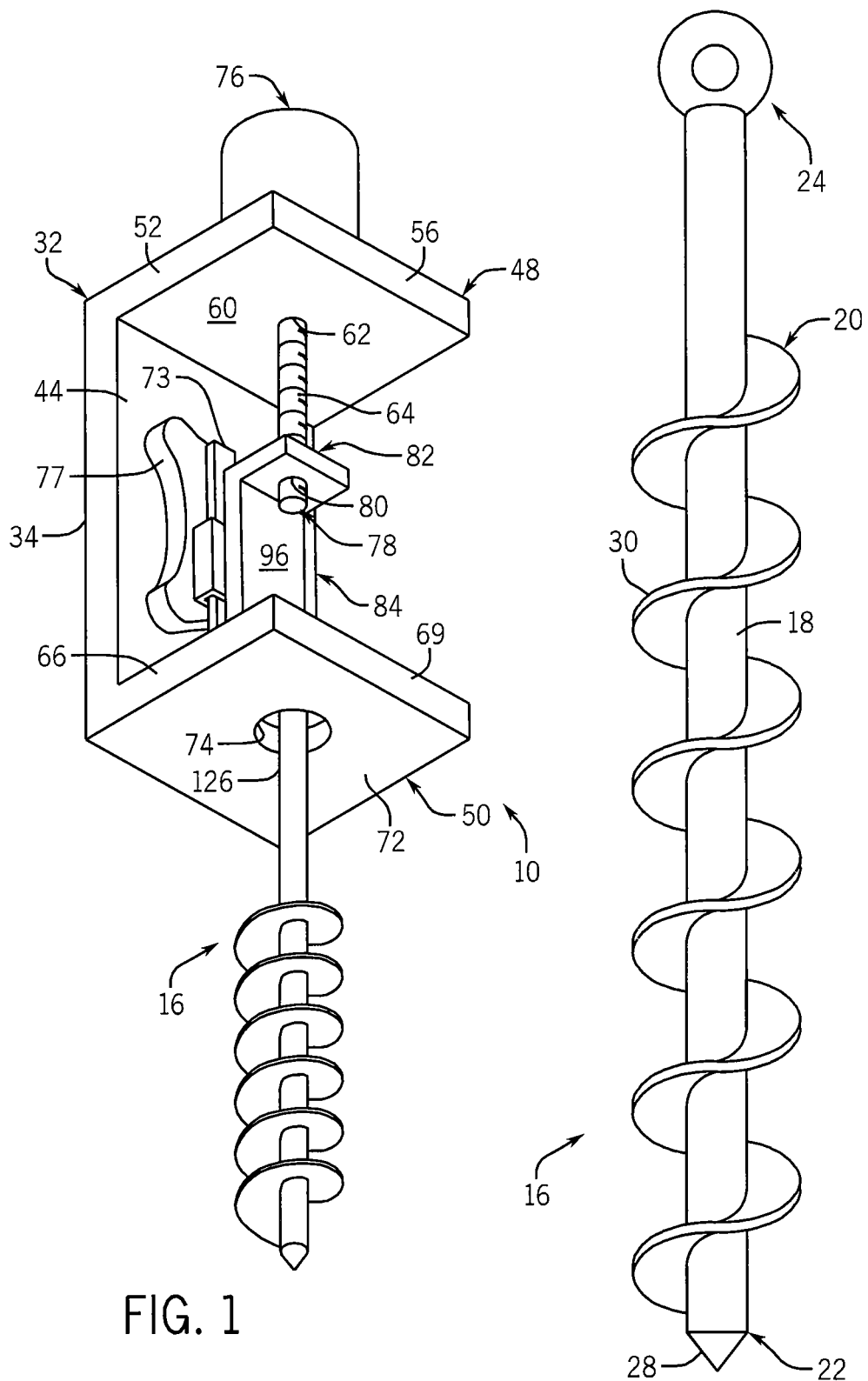

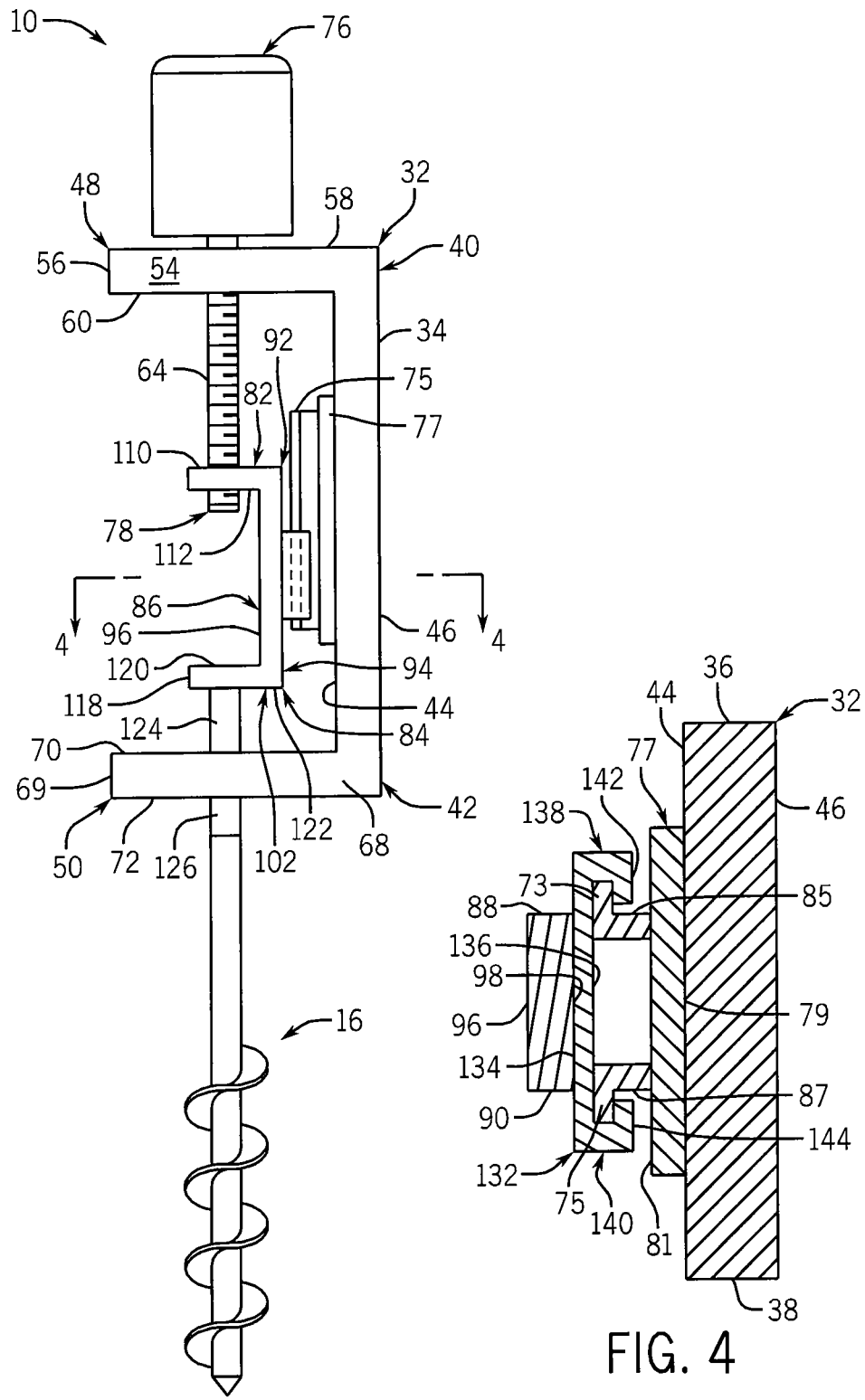

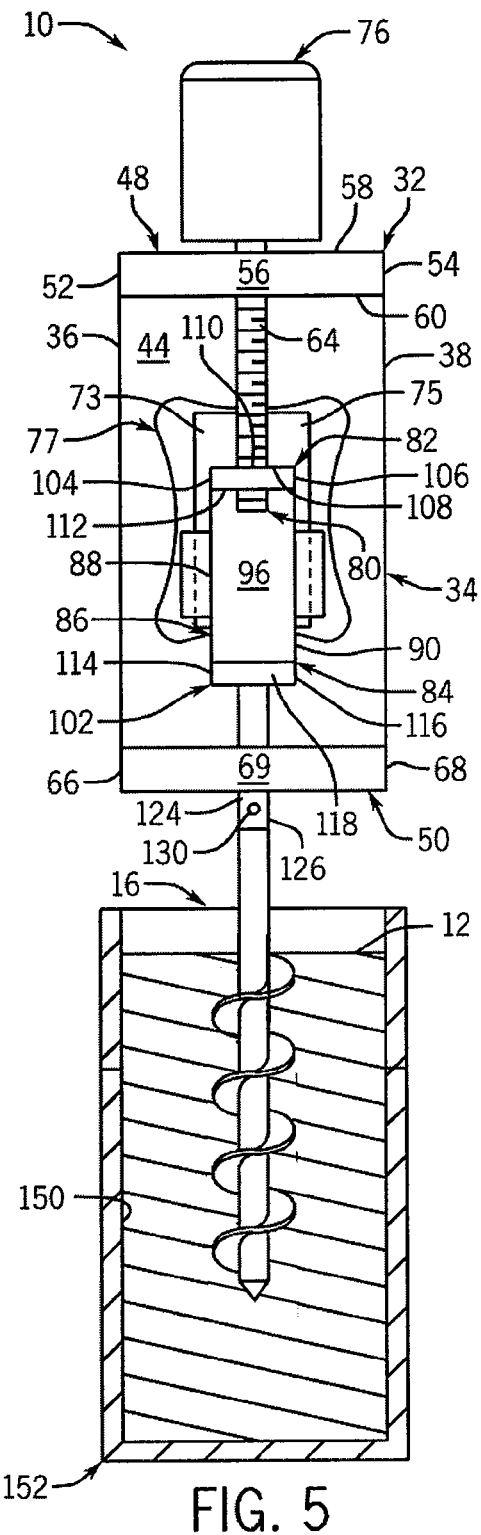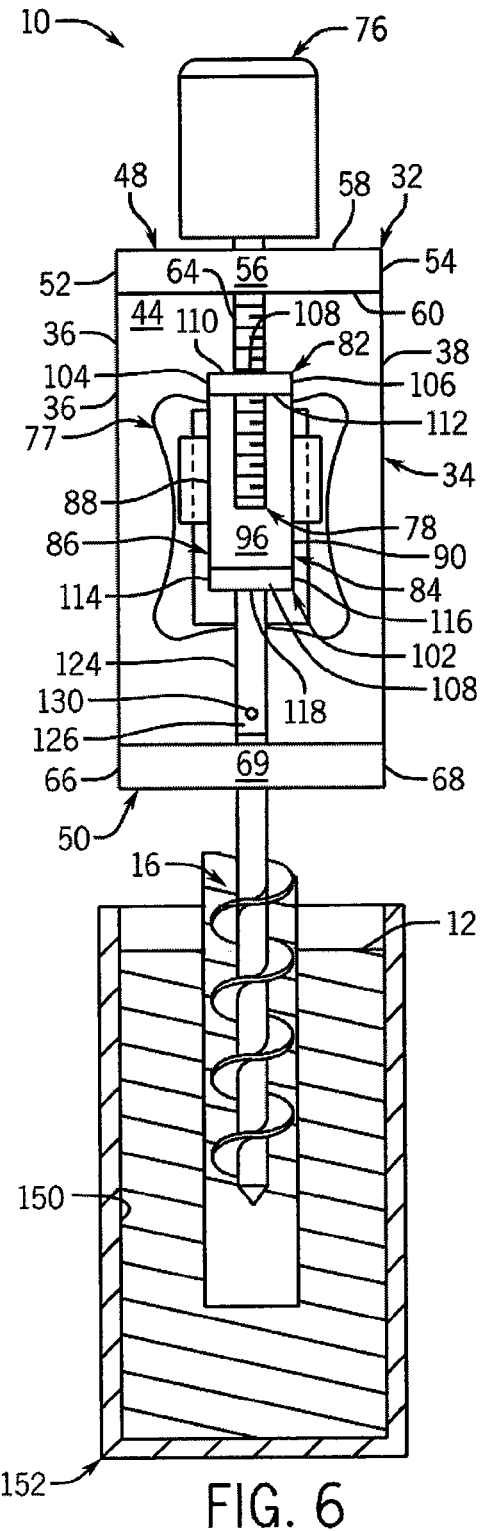

DEVICE AND METHOD FOR MEASURING THE RHEOLOGICAL PROPERTIES OF A YIELD STRESS FLUID

REFERENCE TO GOVERNMENT GRANT

This invention was made with government support under 2010-65504-20406 awarded by the USDA/NIFA. The government has certain rights in the invention.

FIELD OF THE INVENTION

This invention relates generally to fluid flow, and in particular, to a device and a method for measuring the rheological properties of a yield stress fluid, such as biomass material.

BACKGROUND AND SUMMARY OF THE INVENTION

Rising oil prices and the finite nature of fossil fuels have led to an increased demand for alternative fuel sources. One feasible and renewable option is the conversion of biomass material into biofuel. Typically, the conversion process involves the flow of the biomass material through a series of chemical, thermal, and mechanical treatments. Currently, however, generating the flow of the biomass material through the series of treatments is difficult and expensive. Often, significant amounts of auxiliary materials and energy are required to generate the flow of the biomass material through the series of treatments. In order to maximize the efficiency of the conveyance of the biomass material through the series of treatments, and hence reduce the overall cost of generating the biomass flow, the proper design of the industrial processes and equipment is imperative. In order to properly design the industrial processes and equipment, the accurate measurement of the rheological properties of the flow of the biomass material through the series of treatments is necessary.

The most important rheological parameter in the design of industrial processes and equipment is yield stress. Yield stress is the amount of stress that must be exceeded in order to make a structured fluid flow. There are numerous methods for measuring yield stress, ranging from simple practical methods to techniques employing sophisticated rheometers. The most appropriate method can vary from one material to another, as well as, one application to another. Yield stress measurements for biomass material suffer from a number of instrument and material related difficulties, including wall slip, sample ejection, stresses exceeding sensor capacity and sample separation into multiple phases. Measurements are often made using a vane geometry, but this approach is limited to low solids concentrations. Torque rheometry can be used at higher solid concentrations, but this technique can be quite slow (approximately 1.5 hours for a single measurement). Further, both of these approaches utilize apparatuses that are quite expensive, with costs in the range of $50,000-$100,000.

Therefore, it is a primary object and feature of present invention to provide a device and a method for measuring the rheological properties of a yield stress fluid, such as a biomass material, and/or for measuring the rheological properties of other non-Newtonian fluids requiring high stress or special handling.

Therefore, it is a further object and feature of present invention to provide a device and a method for measuring the rheological properties of a yield stress fluid that are simple to operate and inexpensive to manufacture.

Therefore, it is a still further object and feature of present invention to provide a device and a method for measuring the rheological properties of a yield stress fluid that allow a user to quickly receive the results of such measurements.

In accordance with the present invention, a device is provided for measuring a rheological property of a fluid. The device includes an auger having a shaft extending along an axis and a helical flange extending radially about the shaft. The auger is movable in the fluid between a first position and a second position. A sensor is operatively connected to the auger. The sensor measures a force on the auger as the auger moves from the first position to the second position.

A container defines a cavity for receiving the fluid therein. It is contemplated for the sensor to be load cell. The first position and the second position are axially spaced. A positioning structure may operatively connected to the auger. The positioning structure moves the auger between the first and second positions. The positioning structure includes a motor and linkage operatively connecting the motor to the auger. The sensor interconnects the linkage and the auger. A guide structure guides movement of the linkage as the auger is moved between the first and the second positions.

In accordance with a further aspect of the present invention, a device is provided for measuring a rheological property of a fluid. The device includes a container for receiving the fluid therein and an auger. The auger has a shaft extending along an axis and a helical flange extending radially about the shaft. The auger is movable in the fluid between a first position and a second position. A sensor is operatively connected to the auger. The sensor measures a force on the auger as the auger moves from the first position to the second position. Linkage is interconnected to the sensor. The linkage translates motion to the auger.

The sensor may be a load cell and the first position and the second position are axially spaced. A motor is operatively connected to the linkage for imparting axial movement thereon. A guide structure guides movement of the linkage as the auger is moved between the first and the second positions. The auger is releasably connected to the sensor.

In accordance with a still further aspect of the present invention, a method of measuring a rheological property of a fluid is provided. The method includes the steps of threading an auger into a portion of the fluid and interconnecting the auger to a sensor. The sensor generates a signal corresponding to the rheological property of the fluid. The auger is moved in a predetermined direction so as to generate the signal.

The auger has a shaft extending along an axis and a helical flange extending radially about the shaft. The sensor may be a load cell. The step of moving the auger in the predetermined direction includes the step of moving the auger axially between a first position and the second position. Movement of the auger is guided between the first and second positions and the auger is releasably connected to the sensor.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings:

FIG. 1 is an isometric, schematic view of a device for measuring the rheological properties of a yield stress fluid in accordance with the present invention;

FIG. 2 is a side elevational view of an auger of the device of FIG. 1 threaded into a sample fluid;

FIG. 3 is a side elevational view of the device of FIG. 1;

FIG. 4 is a cross sectional view of the device of the present invention taken along line 4-4 of FIG. 3;

FIG. 5 is a side elevational view of the device of FIG. 1 with the auger in a first position;

FIG. 6 is a side elevational view of the device of FIG. 5 with the auger in a second position.

DETAILED DESCRIPTION OF THE DRAWINGS

Figure 7:
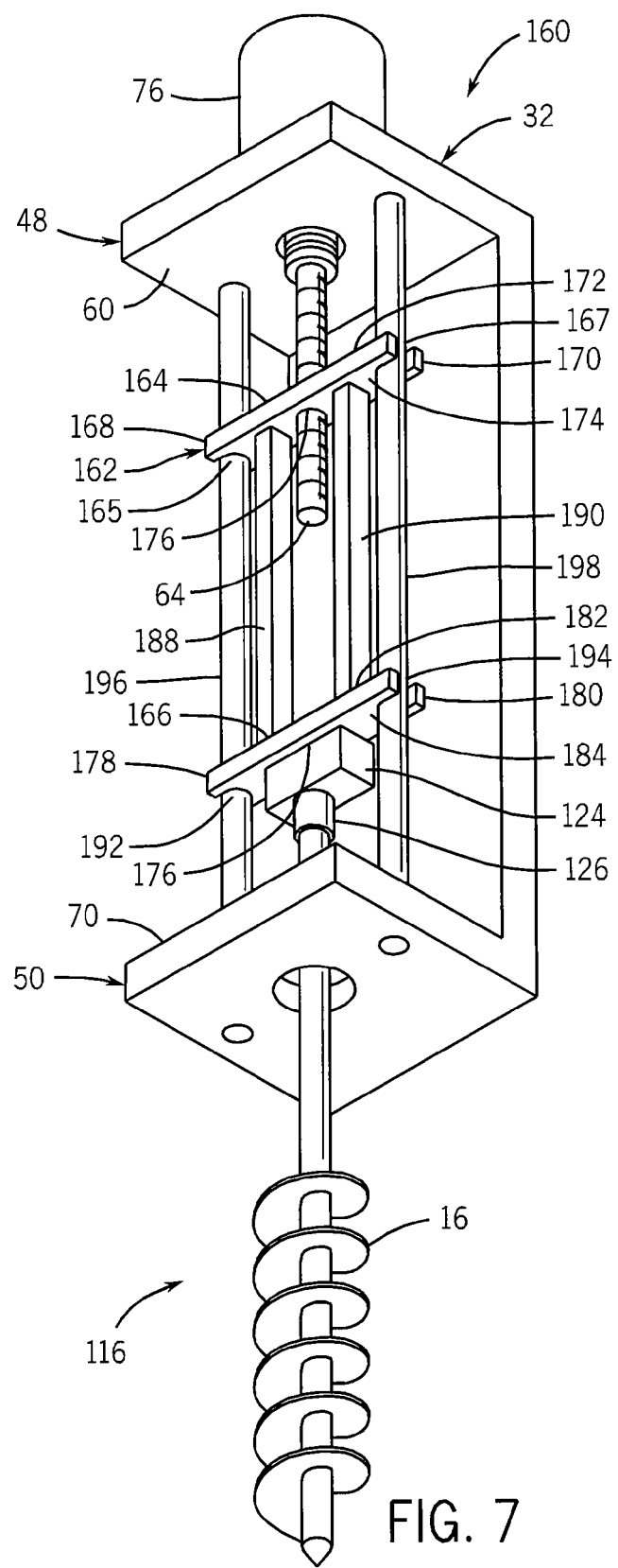
FIG. 7 is an isometric view of an alternate embodiment of a device for measuring the rheological properties of a yield stress fluid in accordance with the present invention.

Referring to FIGS. 1, 3 and 5-6, a device for measuring the rheological properties of a yield stress fluid in accordance with the present invention is generally designated by the reference numeral 10. As hereinafter described, it is intended for device 10 to be used in connection with determining the yield stress of biomass material 12. However, device 10 may be used in connection with determining the yield stress of other types of fluids without deviating from the scope of the present invention.

Device 10 includes auger 16 extending along a longitudinal axis. As best seen in FIG. 2, auger 16 is defined by elongated shaft 18 having first and second opposite ends 20 and 22, respectively. First end 20 of shaft 18 includes a coupling arrangement such as a sleeve, eyelet 24 or the like for releasably connecting auger 16 to load cell 124, for reasons hereinafter described. Second end 22 of shaft 18 terminates at a generally conical surface 28 to facilitate insertion of auger 16 into biomass material 12. Helical-shaped flange 30 extends radially about shaft 18 between first and second ends 20 and 22, respectively, thereof.

Device 10 further includes a generally C-shaped frame 32 defined by generally flat base 34. Base 34 is suitably constructed to rest or mount on the upper end of a sample container 152. By way of example, base 34 is defined by first and second sides 36 and 38, respectively, and first and second ends 40 and 42, respectively. Base 34 is further defined by inner surface 44 and outer surface 46. Upper and lower legs 48 and 50, respectively, project from inner surface 44 of base 34 adjacent corresponding ends 40 and 42 thereof. Upper leg 48 is defined by first and second sides 52 and 54, respectively, which are co-planar with corresponding first and second sides 36 and 38, respectively, of base 34 and terminates at end surface 56. End surface 56 of upper leg 48 is transverse to and interconnects first and second sides 52 and 54, respectively, of thereof. Upper leg 48 is further defined by upper surface 58 and lower surface 60. Aperture 62 extends between upper surface 58 and lower surface 60 of upper leg 48 and accommodates lead screw 64 therethrough.

Lower leg 50 is defined by first and second sides 66 and 68, respectively, which are co-planar with corresponding first and second sides 36 and 38, respectively, of base 34 and terminates at end surface 69. End surface 69 of lower leg 50 is transverse to and interconnects first and second sides 66 and 68, respectively, thereof. Lower leg 50 is further defined by upper surface 70 directed towards lower surface 60 of upper leg 48 and lower surface 72. Lower leg 50 further includes aperture 74 extending between upper surface 70 and lower surface 72 thereof and being in axial alignment with aperture 62 through upper leg 48. It is contemplated for aperture 74 to be of sufficient dimension to accommodates first end 20 of shaft 18 of auger 16 therethrough.

It is contemplated to interconnect generally parallel guide tracks 73 and 75 along inner surface 44 of base 34. More specifically, inner surface 79 of mounting plate 77 is position against and secured to inner surface 44 of base 34 in any conventional manner, FIG. 4. Guide tracks 73 and 75 extend along outer surface 81 of mounting plate 77 and are generally parallel to each other and to base 34 and lead screw 64, For reasons hereinafter described. It is intended for guide tracks 73 and 75 to define corresponding grooves 85 and 87 for slideably receiving guides 142 and 144 of carriage 132 therein.

Drive motor 76 is supported on upper surface 58 of upper leg 48 of frame 32 and includes rotatable lead screw 64 projecting therefrom. It is intended for drive motor 76 to be operatively connected to a controller (not shown) for controlling rotational and axial movement of lead screw 64. Lead screw 64 extends through aperture 62 in upper leg 48 and has a threaded terminal end 78 adapted for receipt in thread bore 80 in upper leg 82 of linkage 84. As hereinafter described, it is intended for linkage 84 to convert the rotary motion of drive motor 76 to linear translation of auger 16 with suitably low frictional resistance so as to not significantly affect the measurement of stress imposed between auger 16 and biomass material 12 in container 152.

Linkage 84 is generally C-shaped and includes a generally flat base 86. Base 86 of linkage 84 is defined by first and second sides 88 and 90, respectively, and first and second ends 92 and 94, respectively. Base 86 is further defined by inner surface 96 and outer surface 98. Generally parallel, upper and lower legs 82 and 102, respectively, project from inner surface 96 of base 86 adjacent corresponding ends 92 and 94 thereof. Upper leg 82 is defined by first and second sides 104 and 106, respectively, which are co-planar with corresponding first and second sides 88 and 90, respectively, of base 86 and terminates at end surface 108. End surface 108 of upper leg 82 is transverse to and interconnects first and second sides 104 and 106, respectively, thereof. Upper leg 82 is further defined by upper surface 110 and lower surface 112. Threaded bore 80 extends between upper surface 110 and lower surface 112 of upper leg 82 and receives lead screw 64 therein, as heretofore described.

Lower leg 102 of linkage 84 is defined by first and second sides 114 and 116, respectively, which are co-planar with corresponding first and second sides 88 and 90, respectively, of base 86 and terminates at end surface 118. End surface 118 of lower leg 102 is transverse to and interconnects first and second sides 114 and 116, respectively, thereof. Lower leg 102 is further defined by upper surface 120 and lower surface 122. Load cell 124 is operatively connected to lower surface 122 of lower leg 102 of linkage 84 in any conventional matter. Load cell 124 includes sleeve 126 depending therefrom which is adapted for receiving eyelet 24 of auger 16 therein. Sleeve 126 includes a threaded bore is adapted for receiving set screw 130 therein in a mating relationship. With eyelet 24 received in sleeve 126, set screw 130 may be threaded into the threaded bore in sleeve 126 such that the terminal end of set screw 130 passes through eyelet 24 thereby connecting auger 16 to load cell 124. It can be appreciated that auger 16 may be releasably connected to load cell 124 in other manners without deviating from the scope of the present invention.

Inner surface 134 of carriage 132 is mounted to outer surface 98 of base 86. Carriage 132 further includes outer surface 136 having first and second generally parallel legs 138 and 140, respectively, projecting therefrom. Guides 142 and 144 extend from the terminal ends of first and second legs 138 and 140, respectively, towards each other. Guides 142 and 144 lie in a common plane and are adapted for slidable receipt in corresponding guide tracks 73 and 75. As described, guides 142 and 144 retain carriage 132, and hence, linkage 84 on guide tracks 73 and 75 and guide axial movement of linkage 84 along the length thereof. It can be appreciated that carriage 132 constrains movement of linkage 84 between drive motor 76 and auger 16 to vertical displacement only.

In operation, biomass material 12 is deposited within interior cavity 150 of container 152. Auger 16 is positioned above cavity 150 and threaded a predetermined distance (e.g. 6 inches) into biomass material 12. Device 10 is positioned on a support (not pictured) such that aperture 74 through lower leg 50 of base 34 is axially aligned with shaft 18 of auger 16. Drive motor 76 of device 10 is actuated such that lead screw 64 rotates in a first direction causing linkage 84 to slide axially downwardly in FIG. 5 along guide tracks 73 and 75, as heretofore described, to a position wherein eyelet 24 of auger 16 may interconnected to sleeve 126 with zero tension provided on load cell 124.

Once auger 16 is operatively connected to load cell 124, drive motor 76 of device 10 is actuated such that lead screw 64 rotates in a second, opposite direction causing linkage 84 to slide axially upward, FIG. 6, along guide tracks 73 and 75. As linkage 84 slides upwardly, auger 16 is pulled perpendicular to surface, thereby generating a force on load cell 124. As is known, load cell 124 generates an electrical signal, mostly commonly a voltage signal, corresponding to the force thereon and provides the same to a measurement circuit (not shown). Typically, the electrical signal corresponds to the force on load cell 124 in kilograms. Linkage 84 continues to be raised by drive motor 76 until such point as the force on load cell 124 reaches a maximum. As is known, yield stress may be calculated according to the expression:

$$YS = YF/(\pi \ast d \ast D) \quad \text{Equation (1)}$$

wherein: YS is the yield stress of the biomass material 12; YF is the maximum force on load cell 124 as the auger 16 is raised less the weight of auger 16; d is the depth of auger 16 in biomass material 12; and D is the diameter of auger 16.

As heretofore described, the depth of auger 16 in biomass material 12 is set by preparation of the experiment and the diameter of auger 16 is constant. As such, the yield stress of the biomass material 12 may be simply and easily calculated in response to the maximum force on load cell 124 and the corresponding electrical signal generated thereby.

Referring to FIG. 7, an alternate embodiment of a device for measuring the rheological properties of a yield stress fluid in accordance with the present invention is generally designated by the reference numeral 160. As described, device 160 is substantially similar to device 10 and includes common elements. Hence, common reference characters are hereinafter used to the common elements of device 160 and device 10.

Linkage 162 includes generally parallel, upper and lower legs 164 and 166, respectively. Upper leg 164 is defined by first and second sides 168 and 170, respectively, upper surface 172 and lower surface 174. Threaded bore 176 extends between upper surface 172 and lower surface 174 of upper leg 164 and receives lead screw 64 therein, as heretofore described. First and second apertures 165 and 167, respectively, extend between upper surface 172 and lower surface 174 of upper leg 164 adjacent corresponding first and second sides 168 and 170, respectively, of upper leg 164.

Lower leg 166 is defined by first and second sides 178 and 180, respectively, upper surface 182 and lower surface 184. Load cell 124 is operatively connected to lower surface 184 of lower leg 166 of linkage 162. Load cell 124 is releasably connectable to auger 16 as heretofore described. Upper surface 182 of lower leg 166 and lower surface 174 of upper leg 164 are interconnected by first and second spaces rods 188 and 190, respectively, positioned on opposite sides of lead screw 64. First and second apertures 192 and 194, respectively, extend between upper surface 182 and lower surface 184 of lower leg 166 adjacent corresponding first and second sides 178 and 180, respectively, of lower leg 166. First and second apertures 192 and 194, respectively, in lower leg 166 are axially aligned with first and second apertures 165 and 167, respectively, of upper leg 166. It is contemplated for first and second guide rods 196 and 198, respectively, to extend between upper surface 70 of lower leg 50 of frame 32 and lower surface 60 of upper leg 48 of frame 32. First guide rod 196 passes through first aperture 192 in lower leg 166 of linkage 162 and first aperture 165 in upper leg 166 of linkage 162. Similarly, second guide rod 198 passes through second aperture 194 in lower leg 166 of linkage 162 and second aperture 167 in upper leg 166 of linkage 162. As described, it is intended for linkage 162 to slide axially along first and second guide rods 196 and 198, respectively. It can be appreciated that first and second guide rods 196 and 198, respectively, constrain movement of linkage 162 between drive motor 76 and auger 16 to vertical displacement only.

In operation, biomass material 12 is deposited within interior cavity 150 of container 152. Auger 16 is positioned above cavity 150 and threaded a predetermined distance (e.g. 6 inches) into biomass material 12. Device 160 is positioned on a support (not pictured) such that aperture 74 through lower leg 50 of base 34 is axially aligned with shaft 18 of auger 16. Drive motor 76 of device 160 is actuated such that lead screw 64 rotates in a first direction causing linkage 162 to slide axially downward along first and second guide rods 196 and 198, respectively, as heretofore described, to a position wherein eyelet 24 of auger 16 may interconnected to sleeve 126 with zero tension provided on load cell 124.

Once auger 16 is operatively connected to load cell 124, drive motor 76 of device 10 is actuated such that lead screw 64 rotates in a second, opposite direction causing linkage 162 to slide axially upward along first and second guide rods 196 and 198, respectively. As linkage 162 slides upwardly, auger 16 is pulled perpendicular to surface, thereby generating a force on load cell 124. Linkage 162 continues to be raised by drive motor 76 until such point as the force on load cell 124 reaches a maximum. Thereafter, the yield stress of the biomass material 12 is calculated, as heretofore described.

In addition to the operation mode heretofore described, it can be appreciated that devices 10 and 160 might operate in other modes, without deviating from the scope of the present invention. By way of example, instead of drawing auger 16 upwardly in biomass material 12, it is contemplated to push auger 16 downwardly into biomass material 12. Further, oscillatory strain and/or the oscillatory stress may be determined at different auger displacement magnitudes or frequencies. In addition, it can be understood that instead of measuring the yield stress as auger 16 is drawn upwardly in biomass material 12, the yield stress may be calculated by measuring the torque on auger 16. Finally, it can be appreciated that by adjusting the auger length, the auger diameter or the container size, rheological measurements on materials of different compositions or yield stress may be accomplished.

Various modes of carrying out the invention are contemplated as being within the scope of the following claims particularly pointing out and distinctly claiming the subject matter, which is regarded as the invention.

We claim:
1. A method of measuring shear yield stress of a fluid, comprising the steps of:
   rotatably threading an auger into a portion of the fluid;
   interconnecting the auger to a sensor, the sensor generating a signal corresponding to a force thereon;

operatively connecting the sensor to a motor with linkage, the motor including a rotatable drive shaft;

rotating the drive shaft of the motor;

converting rotary motion of the drive shaft to linear motion with the linkage such that the linkage displaces the auger linearly along an axis without rotation in a predetermined direction;

determining a point at which the force on the sensor reaches a maximum and generating a maximum force signal in response thereto; and calculating the shear yield stress of the fluid in response to the maximum force signal.

2. The method of claim 1 wherein the auger has a shaft extending along an axis and a helical flange extending radially about the shaft.

3. The method of claim 1 wherein the sensor is a load cell.

4. The method of claim 1 wherein the step of moving the auger in the predetermined direction includes the step of moving the auger axially between a first position and a second position.

5. The method of claim 4 comprising the additional step of guiding movement of the auger between the first and second positions.

6. The method of claim 1 wherein the auger is releasably connected to the sensor.

* * * * *